United States Patent
Rossi et al.

(10) Patent No.: US 10,232,065 B2
(45) Date of Patent: Mar. 19, 2019

(54) ELECTROCHEMICAL DEVICE FOR BIOCIDE TREATMENT IN AGRICULTURAL APPLICATIONS

(75) Inventors: Paolo Rossi, Brugherio (IT); Mariachiara Benedetto, Milan (IT); Luca Buonerba, Milan (IT); Achille De Battisti, Ferrara (IT); Sergio Ferro, Ferrara (IT); Fabio Galli, Cologna (IT)

(73) Assignee: INDUSTRIE DE NORA S.P.A., Milan (IT)

(*) Notice: Subject to any disclaimer, the term of this patent is extended or adjusted under 35 U.S.C. 154(b) by 178 days.

(21) Appl. No.: 12/731,711

(22) Filed: Mar. 25, 2010

(65) Prior Publication Data

US 2010/0183745 A1     Jul. 22, 2010

(51) Int. Cl.
| | |
|---|---|
| *C25C 5/02* | (2006.01) |
| *C25C 7/02* | (2006.01) |
| *C25C 7/06* | (2006.01) |
| *C25B 1/26* | (2006.01) |
| *C25B 9/06* | (2006.01) |
| *C25B 15/02* | (2006.01) |
| *A61L 2/03* | (2006.01) |
| *A61L 2/18* | (2006.01) |

(52) U.S. Cl.
CPC ............ *A61L 2/035* (2013.01); *A61L 2/186* (2013.01); *A61L 2202/11* (2013.01); *A61L 2202/24* (2013.01)

(58) Field of Classification Search
CPC . C02F 1/4618; C25B 1/26; C25B 9/06; C25B 15/02; C25B 1/265; C25C 7/02; C25C 5/02; C25C 7/06
USPC .......................................... 204/242; 205/500
See application file for complete search history.

(56) References Cited

U.S. PATENT DOCUMENTS

| | | | | |
|---|---|---|---|---|
| 2,446,509 | A * | 8/1948 | Fischer | 47/29.1 |
| 4,434,033 | A * | 2/1984 | Kaczur et al. | 205/335 |
| 6,800,257 | B1 * | 10/2004 | Kuriyama et al. | 422/186.3 |
| 7,232,508 | B2 * | 6/2007 | Hosonuma | 204/290.12 |
| 2006/0076248 | A1 * | 4/2006 | Kindred | 205/743 |
| 2006/0147549 | A1 * | 7/2006 | Grab et al. | 424/618 |

FOREIGN PATENT DOCUMENTS

| | | |
|---|---|---|
| JP | 11028397 A | 2/1999 |
| JP | 2003040716 * | 2/2003 |

OTHER PUBLICATIONS

English Translation of Maruyama JP 11-028397.*

* cited by examiner

*Primary Examiner* — Zulmariam Mendez
(74) *Attorney, Agent, or Firm* — Lucas & Mercanti, LLP

(57) ABSTRACT

The invention relates to an electrochemical device which simultaneously carries out the production of an oxidising solution at controlled composition containing hypochlorous acid and the sprinkling thereof in a continuous process, useful for biocide treatments in agricultural fields. The device can be installed on motor vehicles or mobile means in general.

4 Claims, 1 Drawing Sheet

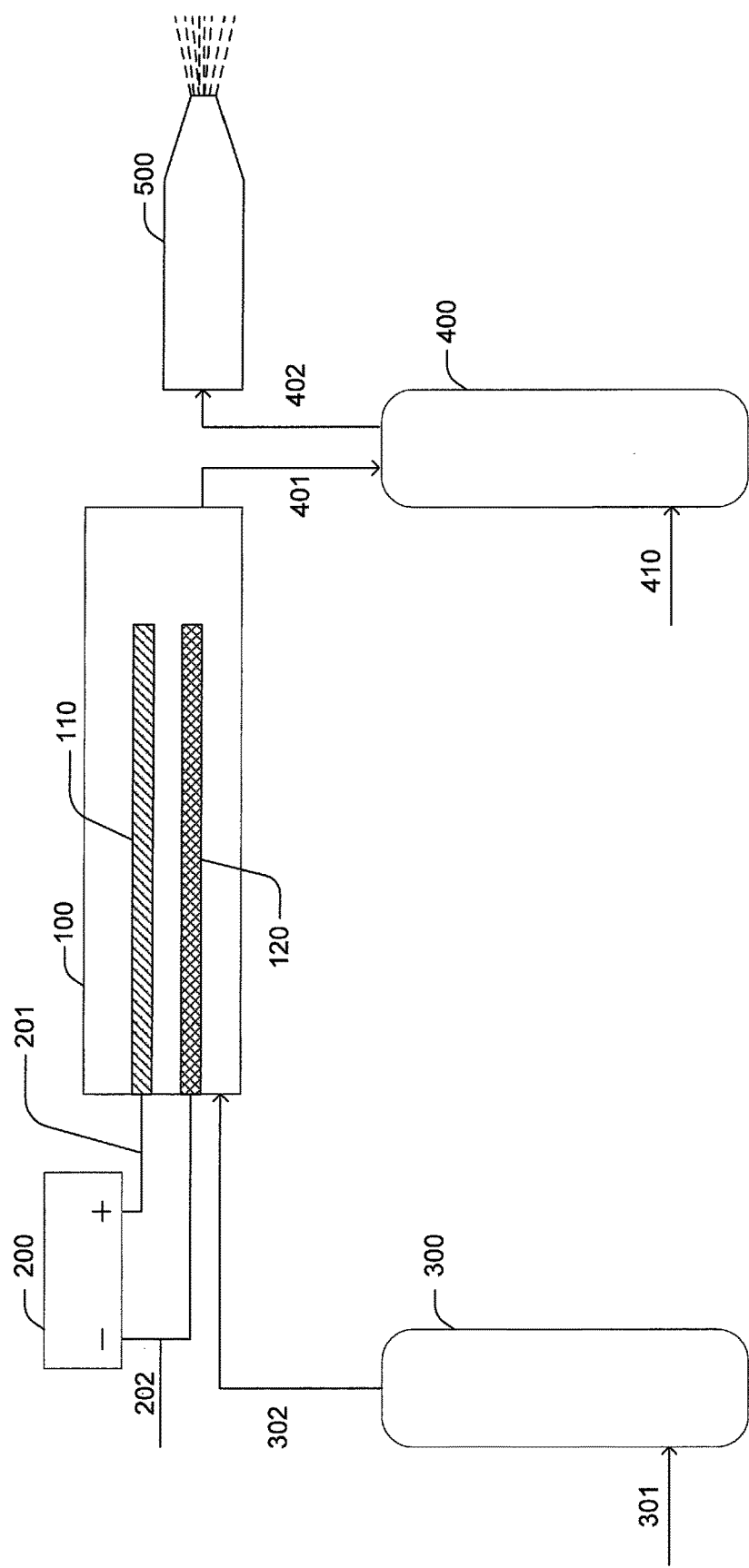

ELECTROCHEMICAL DEVICE FOR BIOCIDE TREATMENT IN AGRICULTURAL APPLICATIONS

FIELD OF THE INVENTION

The invention relates to an electrochemical device for carrying out continuous biocide treatments in agricultural applications by sprinkling of an in situ-produced oxidising solution.

BACKGROUND OF THE INVENTION

The biocide and disinfecting properties of oxidising solutions containing active chlorine under various forms are known in various technical fields. Diluted hypochlorite solutions are used, for instance, in food disinfection and for sterilising tools employed in food processing, hotels and sanitary applications. The use of active chlorine-containing solutions in agricultural applications such as the preventive or therapeutic treatment of microorganism-induced pathologies, on the other hand, is not of common practice, due to the poor efficacy displayed by commercially available products of this kind, that in most of the cases present remarkable drawbacks. In particular, the complex dissociation and disproportioning equilibria whereto chlorine-containing active species are subject, require the use of stabilisers to preserve the nominal composition. For example, the common sodium hypochlorite solutions are stabilised with alkalis, in the simplest case with caustic soda (up to pH 11-12) or with buffered basic solutions (such as sodium tetraborate solutions), in any case at pH not lower than 9.5. Excessively basic solutions are not fit for the direct utilisation in agricultural applications, and also excessive amounts of sodium can pose some problems, as known to those skilled in the art; in particular, biocide solutions fit for sprinkling vegetal species should have a pH not higher than 9, and preferably comprised between 6 and 8.

A very effective source of active chlorine in this pH range is hypochlorous acid, whose biocide properties are known in the art, and which presents the further advantages, compared to commonly employed disinfectants, of being extremely cheap and of releasing no toxic or noxious residues. The use of hypochlorous acid is, nevertheless, hindered by practical reasons, mainly associated with its limited stability which reduces the allowed storage time below levels of practical utility. Moreover, concentrations suitable for an effective use without harmful side-effects for the cultivations (0.01 to 2 g/l) would imply either the packaging and handling of an extremely diluted product, entailing the use of excessive volumes, or the need of diluting the product each time, an operation which, besides being impractical, is also questionable due to the risk of accidentally contaminating the product with substances, for instance metals, that could further reduce its already limited stability.

For this reason, the biocide treatments for the prevention and cure of pathologies induced by microorganisms such as fungi and bacteria are currently carried out by means of a great variety of chemical agents which release toxic residues to the environment and have an often considerable cost.

It would, therefore, be desirable to provide an inexpensive and effective source of active chlorine for biocide treatments in agricultural applications, suitable, for example, in preventive or therapeutic treatment of vegetable pathologies induced by microorganisms such as fungi or bacteria.

SUMMARY OF THE INVENTION

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As provided herein, the invention comprises an electrochemical device for the execution of biocide treatments, having at least one electrolysis cell fed with an alkali chloride solution and comprising at least one anode and at least one cathode, wherein the alkali chloride solution comprises a mixture of sodium chloride and potassium chloride at an overall concentration comprised between 1 and 50 g/l and at a pH comprised between 6 and 8, means for keeping an electrical potential between the anode and the cathode suitable for producing an oxidising solution containing hypochlorous acid; and means for sprinkling the solution.

To the accomplishment of the foregoing and related ends, the following description sets forth certain illustrative aspects and implementations. These are indicative of but a few of the various ways in which one or more aspects may be employed. Other aspects, advantages, and novel features of the disclosure will become apparent from the following detailed description.

BRIEF DESCRIPTION OF THE DRAWING

FIG. 1 is a schematic illustration of one embodiment of the electrochemical device according to the invention, suitable for being used on fixed installations or mounted on a vehicle.

DETAILED DESCRIPTION

In one embodiment, the invention relates to an electrochemical device allowing the continuous execution of biocide treatments in agricultural applications by sprinkling of an in situ-produced oxidising solution containing hypochlorous acid. The device comprises an electrolytic cell fed with a solution of alkali chlorides, comprising, in one embodiment, sodium or potassium chloride or a mixture of the two, which is electrolysed by applying a voltage between the anode and the cathode of the electrolytic cell, with consequent production of an oxidising solution that can be sprinkled on the vegetable species to be treated either directly or following an optional dilution inside the same device.

In one embodiment, a suitable composition for the oxidising solution produced by means of the electrochemical device comprises a hypochlorous acid at a concentration of 0.01 to 2 g/l and at a pH lower than 9, for exampled between 6 and 8. The electrolytic cell of the electrochemical device may be operated so as to directly produce an oxidising solution with the above characteristics. As an alternative, the electrochemical device can be provided with a storage vessel, and the electrolytic cell may be operated so as to produce an oxidising solution at higher concentration, to be subsequently sent to the storage vessel. In this case, the storage vessel can also be fed with a flow of water, optionally at controlled pH, in order to reach the required composition upstream the sprinkling. For this purpose, the electrochemical device can be equipped with means for monitoring hypochlorous acid concentration, pH and temperature, as known in the art.

In one embodiment, the alkali chloride solution fed to the electrolytic cell of the electrochemical device contains sodium and potassium chloride at a concentration of 1 to 50 g/l and a pH comprised between 6 and 9, optionally between 6 and 8.

The production of an oxidising solution by means of the electrochemical device such as herein described can offer the possibility of adjusting the amount of released sodium, depending on the characteristics of the soil and of the vegetal species to be treated. For soils already rich in potassium or cultivations with a relatively high sodium tolerance, the electrochemical device can be fed with cheaper sodium chloride. In other cases, for example if the sodium supply has to be limited, the electrochemical device can be operated with a feed mainly or exclusively comprising a potassium chloride solution.

The oxidising solution obtained by means of the electrochemical device has a higher efficacy compared to the active chlorine-containing commercial products in several treatments of vegetal pathologies induced by microorganisms, in particular by fungi and bacteria, as it contains a particularly active species such as hypochlorous acid at suitable pH, whose concentration is extremely well controlled because its production is simultaneous with the use. The particularly high activity of hypochlorous acid in this kind of application is perhaps justified by its peculiar nature of simultaneous source of nascent oxygen and active chlorine, according to the equilibrium:

$$2HClO \leftrightarrow O_2 + 2HCl$$

$$HClO + HCl \leftrightarrow Cl_2 + H_2O$$

Moreover, the hypochlorous acid solution produced by means of the electrochemical device such as herein described, besides containing other chlorine active compounds in accordance with the known chemical equilibria (chlorine dioxide, hypochlorites, chlorites, chlorates) presumably contains also small amounts of hydrogen peroxide, which although hard to detect by analysis due to the strong reactivity of this species with hypochlorous acid (according to $H_2O_2 + HClO \leftrightarrow O_2 + HCl + H_2O$) contribute by virtue of such reaction to nascent oxygen generation, giving rise to a synergistic effect with hypochlorous acid itself.

In one embodiment, the electrochemical device is equipped with an electrolytic cell of the undivided type, for instance with anodes made out of a titanium substrate activated with suitable catalysts capable of conferring an adequate oxidation potential in the operating conditions and cathodes of nickel or steel, which may be also catalytically activated or non-activated. In another embodiment, the electrochemical device is equipped with a cell provided with a separator, for instance a cell with coaxial cathode and anode separated by a ceramic diaphragm.

The anodic activation can comprise a mixture of metal oxides. During the testing phase, anodes activated with catalytic compositions comprising iridium, ruthenium and tin oxide mixtures proved suitable for obtaining oxidising solution of appropriate compositions.

In another embodiment, both anodes and cathodes comprise activated titanium. This can have the advantage of allowing a periodic inversion of the electrical voltage. Such polarity inversion can help destroy calcium carbonate scales deposited on the cathode surface. For this reason, this embodiment can allow operation with salt solutions containing a high-hardness water, without the need of including softening units for calcium abatement in the electrochemical device.

The device such as herein described is suitable for sprinkling in situ-produced oxidising solutions on various vegetable species. It can be employed in fixed or semifixed installations (for instance in irrigation systems equipped with rotating devices) or installed on mobile means of various types, for instance agricultural motor vehicles, for treating large cultivated zones in a limited time. The treatment of vegetable species with an oxidising solution is suitable for instance for treating fruit trees, as a non limiting example affected by fire blight of bacterial origin (pathology caused by *Erwinia amylovora*), valsa canker (caused by *Valsa ceratosperma*) or nectria canker (by *Nectria galligena*). In these cases, the treatment can be carried out both on leaves (for instance in case of fire blight) and on branches, boughs and trunks (for instance in case of valsa canker or nectria canker). Prior to treating the trees, the affected parts can be bandaged with a hydrophilic gauze or tissue. This can have the advantage of increasing the contact efficiency with the oxidising solution, of decreasing the dispersion of product during the application and slowing down the evaporation thereof.

In one embodiment, it is possible to sprinkle a hydrophilic material in form of gauze or tissue by means of the electrochemical device and subsequently apply it to the parts of trees to be treated.

The electrochemical device such as herein described can be used for treating vegetable species other than fruit trees, for example tomato cultivations affected by *Pseudomonas syringae*, a Gram-negative bacterium causing the bacterial speck of tomato.

Although in the following description, reference will be made to an electrochemical device for agricultural use, the electrochemical device such as herein described can also be used for non-agricultural biocide treatments, for example in disinfection processes for different fields of applications, such as the food industry, including but not limited to washing of fresh vegetables; animal breeding, including but not limited to disinfection of water for animal consumption; the hotel industry, including but not limited to sterilisation of linen; medical care, including but not limited to sterilisation of surgical instruments.

FIG. 1 illustrates one embodiment of the electrochemical device according to the invention, comprising an electrolysis cell (100) in which, for the sake of drawing simplicity, one anode (110) and one cathode (120) with no separator in between are shown. As it will be evident to one skilled in the art, the same considerations apply for cells consisting of intercalated planar anode and cathode assemblies, or of coaxial cylindrical anodes and cathodes, optionally with an interposed separator, for instance a ceramic diaphragm or an ion-exchange membrane. Anode (110) is connected to the positive pole (201) of a current rectifier (200) or other suitable means for imposing an electrical voltage, while cathode (120) is likewise connected to the negative pole (202).

In one embodiment, the voltage applied by current rectifier (200) is periodically reversed at a prefixed frequency.

Electrolysis cell (100) is fed with an alkali chloride solution (302) coming from a feed vessel (300) which may be loaded in batch mode from the outside by suitable feeding means (301).

Solution (302), which during the transit between anode (110) and cathode (120) is subjected to an appropriate electrical potential gradient applied by current rectifier (200) undergoes an electrolytic process with formation of a primary oxidising solution containing hypochlorous acid (401) together with other chlorinated species and optional traces of hydrogen peroxide and ozone.

In another embodiment, a separator is interposed between anode and cathode with consequent formation of two separated compartments, and primary oxidising solution (401) is withdrawn from the anodic compartment.

In the illustrated embodiment, primary oxidising solution (401), having a hypochlorous acid concentration higher than the target one, is fed to a service vessel (400) and diluted therein with pure water or with an aqueous solution, optionally at controlled pH, by suitable admission means (410) operated in continuous (for instance with tap or well-water) or in batch mode.

The oxidising solution is thus brought to a final concentration suitable for its use, in one embodiment comprised between 0.01 and 2 g/l of hypochlorous acid. The final product (402) so obtained is sent to suitable sprinkling means (500) for direct application to the vegetable species to be treated.

In another embodiment, no service vessel (400) is provided, and the oxidising solution (401) is produced at a concentration suitable for direct use and sent to sprinkling means (500).

The concentration of primary oxidising solution (401) can be suitably adjusted by acting on the process parameters (composition of chloride feed solution, current intensity, pH) or on the dimensioning of the electrolysis cell (length and spacing of electrodes, electrolyte residence time), as it will be clear to one skilled in the art. In particular, for a given electrolyte flow, the production of hypochlorous acid and active chlorine generally increases at increasing current intensity and at increasing chloride ion concentration in the feed solution (302). The fine tuning of process parameters may be controlled in continuous, by aid of a suitable instrumentation, not shown. For example, the concentration of hypochlorous acid can be monitored by UV spectrophotometry in continuous mode and adjusted by acting on set potential and electrolyte circulation rate parameters. In one embodiment, the electrochemical device is installed on a mobile means, optionally a vehicle for agricultural use.

EXAMPLE 1

An electrochemical device such as illustrated in FIG. 1 was equipped with an undivided electrolysis cell comprising titanium planar anodes activated with a catalytic coating based on Ir, Ru and Sn oxides and non-activated nickel cathodes. The overall anodic surface, equal to the cathodic one, was 600 cm$^2$. The feed vessel was loaded with a solution at neutral pH containing 1 g/l of NaCl and 2.5 g/l of KCl, and the service vessel was loaded with a tap-water stream whose flow-rate was controlled by a downstream UV probe, calibrated so as to detect the concentration of outlet hypochlorous acid by adsorption at 292 nm adjusting the same at a value comprised between 0.10 and 0.15 g/l at sprinkling stage. The outflow of electrolysis cell to the service vessel was adjusted at a flow-rate of 20 l/h.

The device regulated in this way was used for sprinkling the leaves of 50 pear trees of white William variety affected with fire blight, a disease induced by *Erwinia amylovora* bacterium causing stems, leaves and flowers of the plant to turn brown in localised groups. 50 more individual pear trees of the same field affected by the above-indicated disease were treated with cupric sulphate, according to the prior art. Each treatment was repeated once a day, during 10 subsequent days. After the whole treatment cycle, the fire blight occurrences affecting the individuals sprinkled by means of the electrochemical device were less than 50% compared to plants treated with cupric sulphate.

A scanning electron microscope (SEM) analysis prior to the treatment, carried out on leaves of the same individuals apparently not affected by the disease, showed instead a copious presence of bacterial colonies. After the treatment by means of the device of the invention, a second run of the same analysis evidenced a complete absence of bacterial proliferation. On the contrary, the same check carried out on leaves treated with cupric sulphate, although detecting a substantial reduction of the phenomenon, still showed the signs of traces of bacterial colonies. Such an observation demonstrates that the device of the invention can be effectively used for preventive treatments, in addition to therapeutic ones.

EXAMPLE 2

The device of Example 1 was operated in nearly equivalent conditions in a cultivation of apple trees of the Granny Smith variety affected by Valsa canker and Nectria canker, pathologies caused by fungus agents *Valsa ceratosperma* and *Nectria galligena* which manifest on branches, boughs and trunks as cankers with clean and deeply cracked edges. Compared to the test of the preceding example, the service vessel was not fed with tap water, and in order to obtain an equivalent oxidising solution, the electrolyte cell outlet flow-rate was increased at 45 l/h. Before the treatment, the affected parts to be treated were bandaged with several layers of gauze. The sprinkling treatment on trunks, boughs and branches was carried out once a day for 30 days. At the end of this cycle, all cases of treated canker turned out to be dried up and circumscribed, with growth of fresh wood in the trunk part opposite the affected one.

The above description shall not be intended as a limitation the invention, which may be practised according to different embodiments without departing from the scopes thereof, and whose extent is solely defined by the appended claims. Throughout the description and claims of the present application, the term "comprise" and variations thereof such as "comprising" and "comprises" are not intended to exclude the presence of other elements or additives.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

The invention claimed is:

1. A method for reducing or treating microorganism-induced pathologies in vegetable species by in situ sprinkling of an electrochemically-produced oxidizing solution comprising:
    loading an undiluted feed solution into an electrochemical device for the execution of biocide treatment, the undiluted feed solution comprising potassium chloride having a concentration comprising 1-50 g/l and a pH comprising 6-8 prior to undergoing electrolysis, the electrochemical device comprising:
        a feed vessel comprising the undiluted feed solution to be electrolyzed;
        at least one undivided electrolysis cell comprising at least one anode and at least one cathode;
        means for keeping an electrical potential between the anode and the cathode suitable for producing an oxidizing solution containing hypochlorous acid;
        a service vessel for receiving the oxidizing solution containing hypochlorous acid, the service vessel comprising a downstream UV probe calibrated to detect and adjust the concentration of outlet hypochlorous acid to a concentration comprised between 0.01 to 2 g/l; and means for sprinkling the hypochlorous acid solution from the service vessel;

during transit of the undiluted feed solution between the anode and cathode of the electrochemical device, applying an electrical potential between the anode and the cathode of the electrochemical device loaded with the undiluted feed solution in order to carry out electrolysis and producing hypochlorous acid;

transiting the hypochlorous acid to the service vessel downstream to the UV probe for detecting and adjusting the concentration of outlet hypochlorous acid thereby producing an in situ oxidizing solution comprising 0.01 to 2 g/l of hypochlorous acid and trace amount of hydrogen peroxide; and in situ sprinkling the in situ-produced oxidizing solution on the vegetable species to be treated, wherein the microorganisms comprise one or more of *Erwinia amylovora, Valsa ceratosperma, Nectria galligena* or *Pseudomonas syringae*.

2. The method according to claim 1, wherein the microorganism-induced pathologies are selected from the group consisting of bacterial fire blight, bacterial speck and microbial canker.

3. A method for reducing or treating microorganism-induced pathologies in vegetable species by in situ sprinkling of an electrochemically-produced oxidizing solution comprising:

loading an undiluted feed solution into an electrochemical device for the execution of biocide, the undiluted feed solution comprising potassium chloride, sodium chloride or a mixture thereof having a concentration comprising 1-50 g/l and at a pH comprising 6-8 prior to undergoing electrolysis, the electrochemical device comprising:

a feed vessel comprising the undiluted feed solution to be electrolyzed;

at least one divided electrolysis cell comprising at an anode in an anodic compartment, a cathode in a cathodic compartment and a separator between the anodic compartment and the cathodic compartment;

means for keeping an electrical potential between the anode and the cathode suitable for producing an oxidizing solution containing hypochlorous acid;

a service vessel for receiving the oxidizing solution containing hypochlorous acid, the service vessel comprising a downstream UV probe calibrated to detect and adjust the concentration of outlet hypochlorous acid; and means for sprinkling the hypochlorous acid solution flowing from the service vessel;

during transit of the undiluted feed solution between the anode and the cathode of the electrochemical device, applying an electrical potential in the anodic compartment and the cathodic compartment of the electrochemical device loaded with the undiluted feed solution to produce a primary oxidizing solution in the anodic compartment comprising hypochlorous acid having a concentration higher than 0.01 to 2 g/l;

withdrawing the primary oxidizing solution from the anodic compartment;

feeding the primary oxidizing solution into the service vessel to dilute with water or an aqueous solution and during transit inside the service vessel downstream the UV probe controlling and adjusting the concentration of outlet hypochlorous acid to obtain an in situ-oxidizing solution comprising hydrogen peroxide and 0.01 to 2 g/l of hypochlorous acid; and sprinkling the produced in situ-oxidizing solution on the vegetable species thereby providing synergistic effect of the hydrogen peroxide and hypochlorous acid, wherein the microorganisms comprise one or more of *Erwinia amylovora, Valsa ceratosperma, Nectria galligena* or *Pseudomonas syringae*.

4. The method according to claim 3, wherein the microorganism-induced pathologies are selected from the group consisting of bacterial fire blight, bacterial speck and microbial canker.

* * * * *